United States Patent
Liggett

(10) Patent No.: US 6,498,009 B1
(45) Date of Patent: *Dec. 24, 2002

(54) β-ADRENERGIC RECEPTOR POLYMORPHISMS

(75) Inventor: Stephen Bryant Liggett, Cincinnati, OH (US)

(73) Assignee: University of Cincinnati, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/948,643

(22) Filed: Oct. 10, 1997

(51) Int. Cl.$^7$ ............................ C12Q 1/68; C12P 19/34; C07H 21/04

(52) U.S. Cl. .................. 435/6; 435/91.2; 536/23.5; 536/24.3; 536/24.31; 536/24.33

(58) Field of Search .................. 435/6, 91.2, 91.1, 435/91.5, 810; 536/24.3, 24.31, 24.33; 935/8, 77, 78

(56) References Cited

U.S. PATENT DOCUMENTS

| | | | | |
|---|---|---|---|---|
| 4,965,188 A | * | 10/1990 | Mullis et al. | 435/6 |
| 5,679,524 A | * | 10/1997 | Nikiforov et al. | 435/6 |
| 5,766,851 A | * | 6/1998 | Shuldiner et al. | 435/6 |

OTHER PUBLICATIONS

Stratagene pp. 83–90, 1993.*
Reihsaus et al., Am. J. Respir. Cell Mol. Biol. 8:334–339, Mar. 1993.*
Green et al., Am. J. Respir. Cell Mol. Biol. 13:25–33, Jul. 1995.*
Frielle et al., P.N.A.S, USA 84:7920–7924, Nov. 1987.*
Thon. Mutation Research 285:125–144, Jan. 1993.*
Berrettini et al Nucl. Acids Res. 16:7754, Aug. 1988.*
Turki et al. P.N.A.S., USA 93:10483–10488, Sep. 1996.*
Goodman and Gilman's *The Pharmacological Basis of Therapuetics,* Pergamon Press, 1990, New York, pp. 89–90.
Bristow et al., *Circulation Research* 59:297–309, 1986.
Liggett, S.B., L.E. Wagoner, L.L. Craft, R.W. Hornung, B.D. Hoit, T.C. McIntosh, R.A., Walsh. The Ile164 β$_2$–adrenergic receptor polymorphism adversely affects the outcome of congetive heart failure. J. Clin Invest 102:1534–1539, 1998.
Timmermann, B., R. Mo, F.C. Luft, E. Gerdts, A. Busjahn, P. Omvik, G.–H. Li, H. Schuster, T.F. Wienker, M.R. Hoehe, and P. Lund–Johansen. 1998. β–2 Adrenoceptor genetic variation is asociated with genetic predisposition to essential hypertension: The Bergen Blood Pressure Study, *Kidney International* 53:1455–1460.

Gratze, G., J. Fortin, R. Labugger, A. Binder, P. Kotanko, B. Timmermann, F.C. Luft, M.R. Hoehe, and F. Skrabal. 1999 β–2 Adrenergic Receptor Variants Affect Resting Blood Pressure and Agonist–Induced Vasodilation in Young Adult Caucasions. *Hypertension* 33:1425–1430.
Ishiyama–Shigemoto, S., K. Yamada, X. Yuan, F. Ichikawa, and K. Nonaka. 1999, Association of polymorphisms in the β2–adrenergic receptor gene with obesity, hypertriglyceridaemia, and diabetes mellitus. *Diabetologia* 42:98–101.
Large, V., L. Hellströam, S. Reynisdottir, F. Lönnqvist, P. Eriksson, L. Lannfelt, and P. Arner. 1997. Human Beta–2 Adrenoceptor Gene Polymorphisms are Highly Frequent in Obesity and Associate with Altered Adipocyte Beta–2 Adrenoceptor function. *J. Clin Invest* 100:3005–3013.
Arner, P. and J. Hoffstedt. 1999. Adrenoceptor genes in human obesity. *Journal of Internal Medicine* 245:667–672.
Sakane, N., T. Yoshida, T. Umekawa, A. Kogure, and M. Kondo. 1999. β$_2$–adrenoceptor gene polymorphism and obesity. *Lancet* 353:1976.
Meirhaeghe, A., N. Helbecque, D. Cottel, and P. Amouyel. 1999. β$_2$–adrenoceptor gene polymorphism, body weight, and physical activity. *Lancet* 353:896.
Hellström, L., V. Large, S. Reynisdottir, H. Wahrenberg, and P. Arner. 1999. The different effects of a Gln27 Glu β$_2$–adrenoceptor gene polymorphism on obesity in males and in females. *Journal of Internal Medicine* 245:253–259.
Mason, D.A., J.D. Moore, S.A. Green, and S.B. Liggett. 1999. A gain–of–function polymorphism in a G–protein coupling domain of the human β$_1$–adrenergic receptor. *J Biol Chem* 274:12670–12674.
Moore, J.D., D.A. Mason. S.A. Green, J.Hsu, and S.B. Liggett. 1999. Racial differences in the frequencies of cardiac β$_1$–adrenergic receptor polymorphisms: analysis of c145A>G and c1165G>C. *Hum Mutat* 14:271.
Tesson, F., P. Charron, M. Oeuchmaurd, V. Nicaud, F. Cambien, L. Tiret, O. Poirier, M. Desnos, Y. Jullieres, P. Amouyel, G. Roizes, R. Dorent, K. Schwartz, and M. Komajda. 1999. Characterization of a Unique Genetic Variant in the β$_1$–adrenoceptor gene and Evaluation of its Role in Idiopathic Dilated Cardiomyopathy. *J Mol Cell Cardiol* 31:1032.
Maqbool, A. Hall, M.A., S.G. Ball, and A.J. Balmforth. 1999. Common polymorphisms of β$_1$ –adrenoceptor: identification and rapid screening assay. *Lancet* 353:897.
Lentes et al., A biallelic DNA polymorphism of the human beta–2–adrenergic receptor detected by Ban I–Adrbr–2, *Nucleic Acids Research,* vol. 16, (1998).

(List continued on next page.)

Primary Examiner—Lisa B. Arthur
(74) Attorney, Agent, or Firm—Kalow & Springut LLP; David A. Kalow; William D. Schmidt

(57) ABSTRACT

The invention concerns polymorphisms in the β$_1$- and the β$_2$-adrenergic receptors. The invention also pertains to methods and molecules for detecting such polymorphisms. The invention further pertains to the use of such molecules and methods in the diagnosis, prognosis, and treatment selection for cardiovascular diseases, obesity, and diabetes.

42 Claims, 2 Drawing Sheets

OTHER PUBLICATIONS

Liggett, S.B. and Lefkowitz, R.J., Adrenergic Receptor–coupled Adenylyl Cylase Systems: Regulation of Receptor Function by Phosphorylation, Sequestration and Downregulation, *Mollecular Pharmacology of Cell Regulation*, 3:71–97 (1994).

Turki et al., Genetic Polymorphisms of the $\beta_2$–Adrenergic Receptor in Nocturnal and Nonnocturnal Asthma, *J. Clin. Invest.* 95:1635–1641 (1995).

Higashi et al., Association of a Genetic Variation in the $\beta_3$–Adrenergic Receptor Gene with Coronary Heart Disease among Japanese, *Biochemical and Biophysical Research Communications* 232:728–730 (1997).

Svetkey et al., Preliminary Evidence of Linkage of Salt Sensitivity in Black Americans at the $\beta_2$–Adrenergic Receptor Locus, *American Heart Association* 29:918–922 (1997).

McQuitty et al., Polymorphism in the human β2 adrenergic receptor gene detected by Restriction Endonuclease digestion with Fnu4HI, *Human Genetics* 93:225 (1994).

Hall et al., Association of Glu 27 $\beta_2$–adrenergic polymorphism with lower airway reactivity in asthmatic subjects, *The Lancet* 345:1213–1214 (1995).

Green et al., A polymorphism of the Human $\beta_2$–Adrenergic Receptor within the Fourth Transmembrane Domain Alters Ligand Binding and Functional Properties of the Receptor, *The Journal of Biological Chemistry* 268:23116–23121 (1993).

Green et al., Amino–Terminal Polymorphisms of the Human $\beta_2$–Adrenergic Receptor Impart Distinct Agonist–Promoted Regulatory Properties, *American Chemical Society* pp. 9414–9419 (1994).

Kotanko et al., Essential Hypertension in African Caribbeans Associates with a Variant of the $\beta_2$–Adrenergic, *American Heart Association, Inc.* pp. 773–776 (1997).

Wagoner et al., Polymorphisms of the $\beta_2$ Adrenergic Receptor ($\beta_2$AR) Affect Exercise Capacity in Patients with Heart Failure, (Abstract) *Circulation* 94:3926–3935 (1996).

\* cited by examiner

β-ADRENERGIC RECEPTOR POLYMORPHISMS

FIELD OF THE INVENTION

The invention relates to gene mutations that predispose an individual to cardiac disease, obesity, and diabetes. More specifically, the present invention relates to specific polymorphisms in the $\beta_1$- and the $\beta_2$-adrenergic receptor genes. The invention further relates to methods and molecules for identifying one or more polymorphisms in the $\beta_1$- or the $\beta_2$-adrenergic receptor genes.

BACKGROUND OF THE INVENTION

Beta adrenergic receptors ($\beta$AR) are the receptors for the endogenous catecholamines, epinephrine (adrenaline) and norepinephrine (noradrenaline). There are at least nine subtypes of adrenergic receptors (H. G. Dohlman et al., *Annu. Rev. Biochem.* 60:653–688 (1991); S. B. Liggett et al., In: *Catecholamines, Bouloux*, ed. W. B. Sounders, London (1993)), of which at least three sub-types are $\beta$-adrenergic receptors.

The $\beta_1$- and $\beta_2$-adrenergic receptors ($\beta_1$AR, $\beta_2$AR) are expressed in many organs in the body, including heart, lung, vascular tissue, and pancreas (S. B. Ligget In: *The Lung: Scientific Foundations*, R. G. Crystal et al. (ed.) Lippincott-Raven Publishers, Philadelphia (1996); J. R. Carstairs et al., *Am. Rev. Respir. Dis.* 132:541–547 (1985); Q. A. Hamid et al., *Eur. J. Pharmacol.* 206:133–138 (1991)). In the heart, one or both of these receptors regulate heart rate and pumping function; in the lung the $\beta$AR regulate airway tone; in the vasculature they regulate vascular tone; in adipose tissue they regulate lipolysis; and in the pancreas they contribute to insulin release. These receptors mediate not only the actions of adrenaline and noradrenaline, but a host of synthetic agonists as well.

The $\beta_1$ adrenergic receptor has been cloned and sequenced (T. Frielle et al., *Proc. Natl. Acad. Sci. (USA)* 84:7920–7924 (1987)). The gene has been localized to chromosome q24-q26 of chromosome 10 (T. L. Yang-Feng et al., *Proc. Natl. Acad. Sci. (USA)* 87:1516–1520 (1990). The human $\beta_1$AR has a deduced amino acid sequence of 477 amino acids and is structurally similar to the $\beta_2$AR in many respects. Only a single polymorphism (identified by restriction fragment length polymorphism analysis (RFLP)) has been reported in the human $\beta_1$AR (W. H. Berrettini, et al., *Nucl. Acids Res.* 16:7754 (1988). To date, polymorphisms resulting in amino acid changes in the $\beta_1$AR protein have not been reported.

The gene encoding the human $\beta_2$AR has also been cloned and sequenced (B. K. Kobilka et al., *Proc. Natl. Acad. Sci. (USA)* 84:46–50 (1987)). It is an intronless gene that has been localized to q31-q32 of chromosome 5. The deduced amino acid sequence consists of 413 amino acids, with seven clusters of hydrophobic residues thought to represent transmembrane spanning domains. The N-terminus is extracellular, containing two sites for asparagine-linked glycosylation. The transmembrane spanning domains are connected by three extracellular and three intracellular loops. The C-terminus is intracellular. Several polymorphisms in the $\beta_2$AR gene sequence have been reported (E. Reihsaus et al., *Am. J. Resp. Cell. Mol. Biol.* 8:334–339 (1993); K.-U. Lentes et al., *Nucleic Acids Res.* 16:2359 (1988); and C. K. McQuitty et al., *Hum. Genet.* 93:225 (1994)).

Polymorphisms in the $\beta_2$AR have been studied in the context of asthma (E. Reihsaus et al., *Am. J. Resp. Cell. Mol. Biol.* 8:334–339 (1993), herein incorporated by reference; K. J. Holroyd et al., *Am. J. Respir. Crit. Care Med.* (Abstract) 151:A673 (1995); D. M. Cooper et al., *Am. J. Respir. Crit. Care Med.* (Abstract) 153:A254 (1996); K. S. Tan et al., *Am. J. Respir. Crit. Care Med.* (Abstract) 155:A208 (1997)). There appears to be no difference in the distribution of $\beta_2$AR polymorphisms between individuals suffering from asthma and normal individuals. There is evidence, however, of an association between one polymorphism and more severe asthma (Reihsaus et al.). More recently, these polymorphisms have been shown to be associated with the nocturnal asthmatic phenotype (J. Turki et al., *J. Clin. Invest.* 95:1635–1641 (1995)), bronchial hyperreactivity (I. P. Hall et al., *The Lancet* 345:1213–1214 (1995)), and IgE levels (J. C. Dewar et al., *J. Allergy Clin. Imm.* (In Press)). Using site directed mutagenesis and recombinant expression in fibroblasts, the pharmacologic properties of these variants have been assessed in vitro (S. A. Green et al., *J. Biol. Chem.* 268:23116–23121 (1993); S. A. Green et al., *Biochemistry* 33:9414–9419 (1994))and in transgenic mice (J. Turki et al., *Proc. Natl. Acad. Sci. (USA)* 93:10483–10488 (1996)).

Given the importance of the $\beta_1$- and the $\beta_2$-adrenergic receptors in modulating a variety of physiological functions, there is a need in the art for improved methods to identify these polymorphisms and to correlate the identity of these polymorphisms with the other functions of $\beta$-adrenergic receptors. The present invention addresses these needs and more by providing polymorphisms, molecules, and methods useful for the diagnosis and prognosis of cardiovascular diseases, obesity, and diabetes.

SUMMARY OF THE INVENTION

Figure 1:
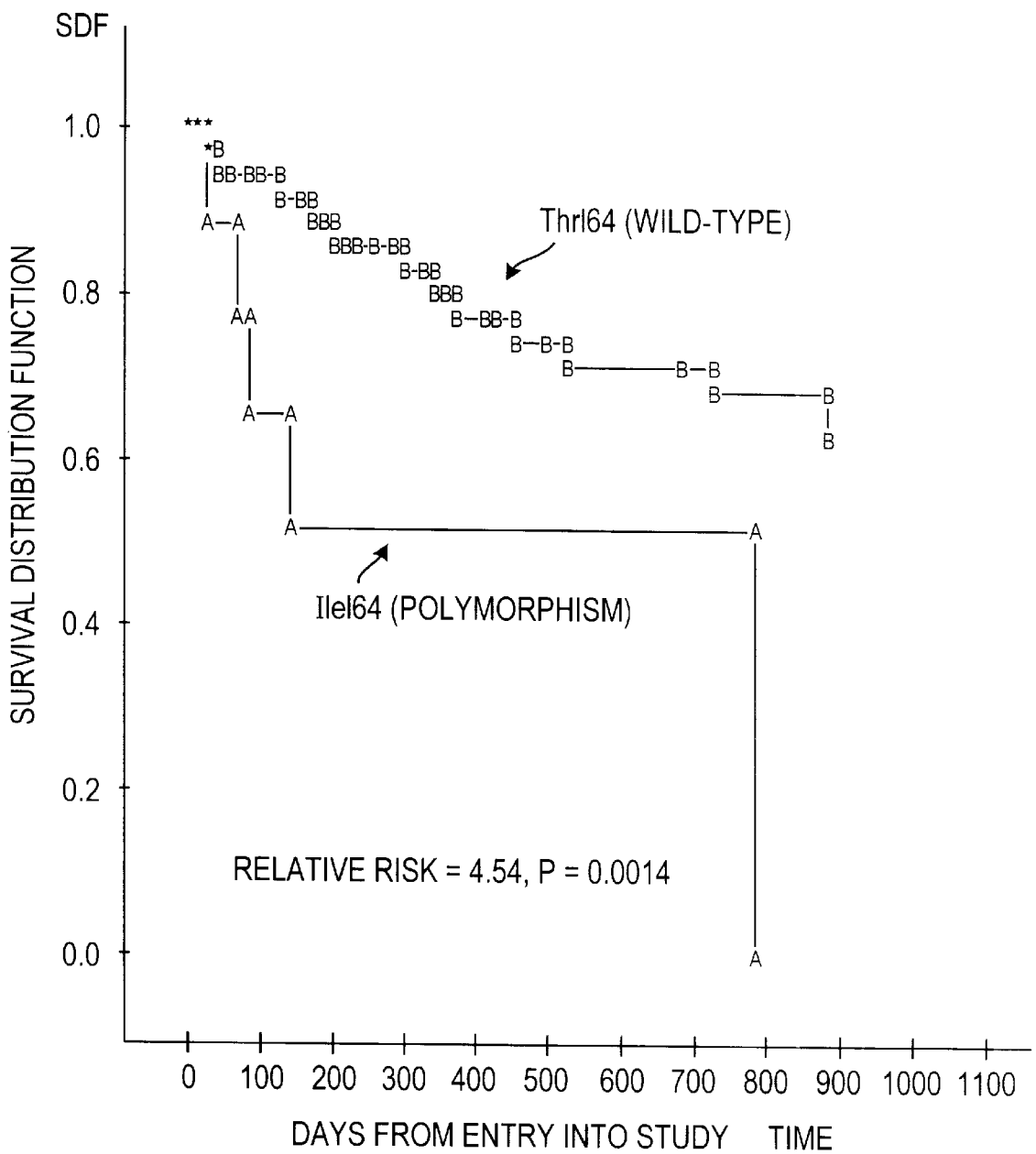
FIG. 1 provides a graph of survival over time in patients with heart failure showing a relationship between survival and identity of the $\beta_2$AR polymorphism at amino acid 164. An experiment enrolling 279 patients with heart failure is shown.

The present invention is directed to molecules useful for determining the identity of one or more polymorphic sites in the $\beta_1$- and the $\beta_2$-adrenergic receptor genes. The invention is also directed to methods for determining the identity of one or more polymorphic sites in the $\beta_1$- and the $\beta_2$-adrenergic receptor genes. In particular, the invention is directed to molecules and methods useful for determining the identity of one or more polymorphic sites in the $\beta_1$- and the $\beta_2$-adrenergic receptor genes and correlating the identity of such sites with a genetic predisposition for a disease. The invention is particularly concerned with a genetic predisposition for cardiovascular diseases including hypertension, congestive heart failure, stroke, myocardial infarction, neurogenic and obstructive peripheral vascular disease, and migraine. The invention is also particularly concerned with a genetic predisposition for obesity and diabetes.

The invention also provides a kit, suitable for genetic testing. Such a kit contains primers for amplifying regions of $\beta$-adrenergic receptor nucleic acid encompassing regions where at least one of the polymorphisms are found. The kit also contains allele-specific oligonucleotides, specific for both mutant and wild-type alleles of at least one of these mutations. The kit may also contain sources of "control" target polynucleotides, as positive and negative controls. Such sources may be in the form of patient nucleic acid samples, cloned target polynucleotides, plasmids or bacterial strains carrying positive and negative control DNA.

In detail, the invention provides anoligonucleotide for determining the identity of a polymorphic site of a beta-1 adrenergic receptor molecule of a target polynucleotide, wherein:
  a) said target polynucleotide comprises a segment of a of a beta-1-adrenergic receptor molecule;
  b) said segment comprises said polymorphic site; and
  c) said oligonucleotide is complementary to said segment.

The invention particulary concerns the embodiments wherein said oligonucleotide comprises said polymorphic site, and said oligonucleotide is an allele-specific oligonucleotide or wherein said oligonucleotide does not comprise said polymorphic site, and said oligonucleotide is a primer oligonucleotide.

The invention further provides such an allele-specific oligonucleotide, wherein said oligonucleotide is complementary to said target polynucleotide at a region comprising or being nucleotide position 145 or 1165 of a coding region of said beta-1-adrenergic receptor molecule The invention further concerns the embodiment in which such oligonucleotide is labeled with a label selected from the group: radiolabel, fluorescent label, bioluminescent label, chemiluminescent label, nucleic acid, hapten, or enzyme label.

The invention further provides a primer oligonucleotide for amplifying a region of a target polynucleotide, said region comprising a polymorphic site of a beta-1-adrenergic receptor molecule (especially one comprising nucleotide positions 145 or 1165 of a coding region of said beta-1-adrenergic receptor molecule, wherein said primer oligonucleotide is substantially complementary to said target polynucleotide, thereby permitting the amplification of said region of said target polynucleotide.

The invention further provides a method for classifying at least one beta-adrenergic receptor molecule of an individual for diagnostic or prognostic purposes, comprising:
  a) isolating from a biological sample from said individual a target polynucleotide comprising at least one beta-adrenergic receptor molecule;
  b) incubating the target polynucleotide in the presence of at least one oligonucleotide, said oligonucleotide being complementary to said target polynucleotide, said target polynucleotide comprising at least one polymorphic site of said beta-adrenergic receptor molecule, wherein said incubation is under conditions sufficient to allow specific hybridization to occur between the target polynucleotide and said oligonucleotide, said specific hybridization thereby permitting the determination of the identity of at least one polymorphic site of said target polynucleotide;
  c) determining the identity of at least one polymorphic site of said target polynucleotide (especially by Genetic Bit Analysis™; and
  d) classifying said beta-adrenergic receptor molecule for said diagnostic and prognostic purposes according to the identity of said polymorphic site.

The invention concerns the embodiments of the above method in which the beta-adrenergic receptor molecule is either beta-1-adrenergic receptor molecule (especially 145 or 1165 of a coding region of said beta-1-adrenergic receptor molecule) or beta-2-adrenergic receptor molecule (especially wherein said polymorphic locus comprises nucleotide position 46, 79, 100 or 491 of said beta-2-adrenergic receptor molecule.

The invention particularly concerns the embodiment, wherein said diagnostic and prognostic purposes are (1) determining risk for the development of cardiovascular diseases selected from the group comprising: hypertension, congestive heart failure, stroke, myocardial infarction, neurogenic peripheral vascular disease, diabetes, obesity, obstructive peripheral vascular disease, and migraine and/or (2) predicting the clinical course of cardiovascular diseases selected from the group comprising: hypertension, congestive heart failure, stroke, myocardial infarction, neurogenic peripheral vascular disease, diabetes, obesity, obstructive peripheral vascular disease, and migraine.

Thus, the invention concerns a method for diagnosing cardiovascular disease, obesity, or diabetes in a patient which comprises the steps:
  (A) incubating under conditions permitting nucleic acid hybridization: an oligonucleotide, said oligonucleotide comprising a nucleotide sequence of a polynucleotide that specifically hybridizes to a polynucleotide that comprises a beta-adrenergic receptor molecule (especially, a beta-1-adrenergic receptor molecule, or a beta-2-adrenergic receptor molecule), and a complementary target polynucleotide obtained from a biological sample of said patient, wherein nucleic acid hybridization between said oligonucleotide, and said target polynucleotide obtained from said patient permits the detection of a polymorphism affecting beta-adrenergic receptor activity in said patient;
  (B) permitting hybridization between said oligonucleotide and said target polynucleotide obtained from said patient; and
  (C) detecting the presence of said polymorphism, wherein the detection of said polymorphism is diagnostic of a disease selected from the group: heart disease, obesity, and diabetes.

The invention further provides a kit for detecting polymorphisms in a $\beta_1$ or a $\beta_2$ adrenergic receptor molecule that comprises:
  (A) a first container containing primers for amplifying regions of a $\beta_1$ or a $\beta_2$ adrenergic receptor molecule; and
  (B) a second container containing primers for detecting said polymorphisms.

DETAILED DESCRIPTION OF THE INVENTION

As indicated above, β-adrenergic receptors play an important role in regulating a variety of physiological functions. The present invention stems in part from the recognition that certain polymorphisms in the $\beta_2$-adrenergic receptor results in receptor molecules with altered functions (S. B. Ligget et al., In: *Molecular Pharmacology of Cell Regulation, Volume 3*, M. D. Houslay (ed.), Wiley & Sonsl (1994); S. A. Green et al., *Biochemistry* 33:9414–9419 (1994); S. A. Green et al., *Am. J. Respir. Cell Mol. Biol.* 13:25–33 (1995)). The same is true for certain polymorphisms in the $\beta_1$-adrenergic receptor. These altered functions can affect both an individual's propensity for, and clinical course of diseases including cardiovascular diseases, obesity, and diabetes. These altered functions can also affect an individual's responsiveness to synthetic agonists and antagonists.

The human heart expresses both the $\beta_1$AR and the $\beta_2$AR subtypes (M. R. Bristow et al., *Mol. Pharmacol.* 35:296–303

(1988)). Each receptor mediates positive inotropic and chronotropic responses to endogenous catecholamines and exogenously administered agonists (E. O. Brodde et al., *J. Cardiovasc. Pharmacol.* 8:1235–1242 (1986); O. E. Brodde et al., *Z. Kardiol.* 81:71–78 (1992)). Depressed $\beta_1$AR and/or $\beta_2$AR function in the heart would predispose heart failure to worsen, since both receptors are critical for the pumping function of the heart. Such would be the case, for example, with the $\beta_2$AR containing the Ile164 polymorphism. Other polymorphisms, however, act in an analogous manner.

Interestingly, at certain times during heart failure, the heart self-regulates the $\beta_1$AR and the $\beta_2$AR by decreasing their expression levels, presumably to protect the heart against being excessively stimulated. $\beta_1$AR expression, in particular, has been noted to be markedly reduced in patients with idiopathic dilated cardiomyopathy, possibly due to elevated catecholamine levels (M. R. Bristow et al., *Circ. Res.* 59:297–309 (1986)). In chronic heart failure, cardiac beta-adrenoceptor function decreases (presumably due to endogenous "downregulation" by the elevated catecholamines) and this decrease is related to the severity of the disease. Given that certain $\beta$AR polymorphisms alter this downregulation pattern in vitro, a worsening heart failure scenario is expected. In addition, most forms of congestive heart failure, including idiopathic forms, are characterized by a diminished responsiveness to $\beta$-agonists.

Because noradrenaline is the main transmitter of the human sympathetic nervous system, under normal physiological conditions, heart rate and contractility are under the control of cardiac $\beta_1$-adrenergic receptors, whereas cardiac $\beta_2$-adrenergic receptors play only a minor role. However, in situations of stress, when large amounts of adrenaline (acting at both $\beta_1$- and $\beta_2$-adrenergic receptors with the same affinity) are released from the adrenal medulla, activation of cardiac $\beta_2$-adrenergic receptors may contribute to an additional increase in heart rate and/or contractility (O. E. Brodde et al., *Z. Kardiol.* 81:71–78 (1992)).

Similar regulatory events occur after myocardial infarction (heart attack), where loss of heart tissue is associated with these adaptive changes in receptors. Under these circumstances, the $\beta_2$AR may take on an even greater role in providing for cardiac responses to increased sympathetic drive or exogenous agonists.

$\beta$-adrenergic receptors also regulate vascular tone, by dilating vessels. Depressed signaling, due to a polymorphic receptor, such as the Gly16 variant, would thus result in higher blood pressures. Such aberrant regulation in the cerebral vessels leads to a predisposition for migraine or stroke as well. Similarly, vasoconstricted vessels would be expected to aggravate neurogenic or atherosclerotic peripheral vascular disease and further limit blood flow. Thus, the altered functions of certain polymorphic variants of the $\beta_1$AR and the $\beta_2$AR would thus affect an individual's predisposition for, or clinical course of cardiovascular diseases.

Both $\beta_1$AR and $\beta_2$AR are critical to glucose and fat metabolism. Both receptors are expressed on adipose cells and augment lipolysis (P. Amer *Am. J. Clin. Nutr.* 55:228S–236S (1992); S. Reynisdottir et al., *Diabetologia* 37:428–435 (1994)). Aberrations in the $\beta_1$AR and the $\beta_2$AR, such as are found with the Ile164, Gly16, or Gln27 polymorphic variants of the $\beta_2$AR, for example, would thus diminish lipolysis and lead to obesity.

Insulin secretion in the pancreas is under partial control of the $\beta_2$AR, as is glucose metabolism due to the expression of the receptor in skeletal muscle. The altered $\beta_2$AR functions of certain polymorphic variants would thus predispose an individual to, or worsen diabetes mellitus, especially in combination with obesity.

These conclusions are further supported by a recent publication by Turki, et al. (J. Turki et al., *Proc. Natl. Acad. Sci.* (*USA*) 93:10483–10488 (1996)). Turki et al. demonstrated a myocardial signaling defect in transgenic mice carrying a mutated human $\beta_2$AR. Transgenic mice were created that contained a $\beta_2$AR that had been altered by site-directed mutagenesis to contain an isoleucine at the polymorphic site at amino acid 164. Turki et al. found that the mutated $\beta_2$AR had a significant affect on receptor coupling. The study is somewhat limited, however, in that both wt-$\beta_2$AR and the Ile164 polymorphic variant were expressed against a background of endogenous mouse $\beta$-adrenergic receptors.

In addition, L. E. Wagoner et al. recently reported a weak association between certain $\beta_2$AR polymorphisms and exercise capacity in patients with heart failure (L. E. Wagoner et al., *Circulation* 94:8(Abstract) (Oct. 15, 1996)). The usefulness of $\beta_1$- and $\beta_2$-polymorphisms as predictors for the development or clinical course of a cardiovascular disease is not addressed, though exercise capacity may be a component of the clinical course of congestive heart failure.

In a recent paper, Higashi, et al. observed an apparent association between certain polymorphisms of the $\beta_3$-adrenergic receptor and coronary heart disease among Japanese nationals (Higashi, et al. *Biochem. Biophys. Res. Comm.* 232:728–730 (1997)). Higashi et al. found that there was a statistically significant correlation between patients with coronar be art disease and a Trp64Arg mutation in the gene for the $\beta_3$-adrenergic receptor. The $\beta_3$-adrenergic receptor, however, is a different molecule than the $\beta_1$AR and the $\beta_2$AR and, in fact, Higashi et al. does not discuss the $\beta_1$AR, the $\beta_2$AR, polymorphisms in these receptors, or suggest any relationship to either of these receptors and a cardiovascular disease, obesity, or diabetes. In contrast to the $\beta_1$AR and the $\beta_2$AR, the $\beta_3$AR is primarily expressed in visceral fat in humans and regulates thermogenesis and lipolysis in brown adipose tissue (S. Krief et al., *J. Clin. Invest.* 91:344–349 (1993); N. J. Rothwell et al, *Nature* 281:31–35 (1979); P. Trayhurn et al., *Biochem. Soc. Trans.* 14:236–239 (1986)). $\beta_3$-adrenergic receptor agonists have an anti-obesity and anti-diabetic effects (B. Lowell et al., *J. Clin. Invest.* 95:923 (1995); J. Himms-Hagen et al., *Am. J. Physiol.* 266:1371–1382 (1994); S. Tsujii et al, *Brain Res.* 587:226–232 (1992); T. Yoshida et al., *Life Sciences* 54:491–498 (1994)).

I. Polymorphisms of the Present Invention

The particular gene sequences of interest to the present invention comprise "mutations" or "polymorphisms" in the genes for the $\beta_1$-adrenergic receptor ($\beta_1$AR) and the $\beta_2$-adrenergic receptor ($\beta_2$AR).

The genomes of animals and plants naturally undergo spontaneous mutation in the course of their continuing evolution (J. F. Gusella *Ann. Rev. Biochem.* 55:831–854 (1986)). These mutations may be in the form of deletions, insertions, or base changes at a particular site in a nucleic acid sequence. The altered sequence and the initial sequence may co-exist in a species' population. In some instances, these changes confer neither an advantage or a disadvantage to the species and multiple alleles of the sequence may be in stable or quasi-stable equilibrium. In some instances, however, these sequence changes will confer a survival or evolutionary advantage to the species, and accordingly, the altered allele may eventually (i.e. over evolutionary time) be incorporated into the genome of many or most members of that species. In other instances, the altered sequence confers a disadvantage to the species, as where the mutation causes or predisposes an individual to a genetic disease. As used herein, the terms "mutation" or "polymorphism" refer to the condition in which there is a variation in the DNA sequence between some members of a species. Typically, the term "mutation" is used to denote a polymorphism that results in the gene coding for a non-functioning protein or a protein with a substantially altered or reduced function or that additionally contributes to a disease condition.

A polymorphism is thus said to be "allelic," in that, due to the existence of the polymorphism, some members of a species carry a gene with one sequence (e.g., the original or wild-type "allele"), whereas other members may have an altered sequence (e.g., the variant or mutant "allele"). In the simplest case, only one mutated variant of the sequence may exist, and the polymorphism is said to be diallelic. The occurrence of alternative mutations can give rise to triallelic polymorphisms, etc. An allele may be referred to by the nucleotide(s) that comprise the mutation.

The terms "$\beta_1$-adrenergic receptor" polymorphisms or "$\beta_1$AR" polymorphisms, therefore, are terms of art and refer to polymorphisms in the nucleic acid or amino acid sequence of a $\beta_1$-adrenergic receptor gene or gene product. For reference purposes only, GenBank Accession No. J03019 and PO8588 (both herein incorporated by reference) are examples of a wild-type $\beta_1$-adrenergic receptor gene sequence. For the purposes of identifying the location of a polymorphism, the first nucleotide of the start codon of the coding region; (the adenine of the ATG in a DNA molecule and the adenine of the AUG in an RNA molecule) of the $\beta_1$AR gene is considered nucleotide "1." Similarly, the first amino acid of the translated protein product (the methionine) is considered amino acid "1."

Similarly, the terms "$\beta_2$-adrenergic receptor" polymorphisms or "$\beta_2$AR" polymorphisms are also terms of art and refer to the polymorphisms in the nucleic acid or amino acid sequence for the $\beta_2$-adrenergic receptor gene or gene product. For reference purposes only, GenBank Accession No. M15169 (herein incorporated by reference) is an example a wild-type $\beta_2$-adrenergic receptor gene sequence. For the purposes of identifying the location of a polymorphism, the first nucleotide of the start codon of the coding region (the adenine of the ATG in a DNA molecule and the adenine of the AUG in an RNA molecule) of the $\beta_2$AR gene is considered nucleotide "1." Similarly, the first amino acid of the translated protein product (the methionine) is considered amino acid "1."

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to the sense strand, only for the purpose of convenience.

Preferred polymorphisms and polymorphic sites in a gene for a $\beta_1$AR include the following:

TABLE 1

$\beta_1$-Adrenergic Receptor Polymorphisms

| Nucleotide Position | Nucleotide | Amino Acid Position | Amino Acid | Designations |
|---|---|---|---|---|
| 145 | A or G | 49 | Ser or Gly | Ser49, Gly49 |
| 1165 | G or C | 389 | Gly or Arg | Gly389, Arg389 |

It is believed that above-listed polymorphisms in the $\beta_1$AR have not been previously reported. Wild-type $\beta_1$AR nucleotide sequences generally comprise an adenine at nucleotide 145 and a guanine at nucleotide 1165. Wild-type $\beta_1$AR protein sequences generally comprise a serine at amino acid 49 and a glycine at amino acid 389.

Preferred polymorphisms and polymorphic sites in a gene for a $\beta_2$AR include the following:

TABLE 2

$\beta_2$-Adrenergic Receptor Polymorphisms

| Nucleotide Position | Nucleotide | Amino Acid Position | Amino Acid | Accession Number | Designations |
|---|---|---|---|---|---|
| 46 | A or G | 16 | Arg or Gly | AF022953 | Arg16→Gly, Arg16, Gly16 |
| 79 | C or G | 27 | Gln or Glu | AF022954 | Gln27→Glu, Gln27, Glu27 |
| 100 | G or A | 34 | Val or Met | AF022955 | Val34→Met |
| 491 | C or T | 164 | Thr or Ile | AF022956 | Thr164→Ile, Thr164, Ile164 |

The preferred polymorphisms of the present invention that occur in the $\beta_2$AR have been previously described (E. Reihsaus et al., *Am. J. Resp. Cell. Mol. Biol.* 8:334–339 (1993)). Wild-type $\beta_2$AR nucleotide sequences generally comprise an adenine, a cytosine, a guanine, and a cytosine at nucleotides 46, 79, 100, and 491, respectively. Wild-type $\beta_2$AR protein sequences generally comprise an arginine, a glutamine, a valine, and a threonine at amino acids 16, 27, 34, and 164, respectively.

The Molecules of the Present Invention

The molecules of the present invention are particularly relevant to the diagnosis and prognosis of cardiovascular diseases, obesity, and diabetes. As used herein, the terms "obesity" and "diabetes" have their art-recognized meanings. As used herein, the term "cardiovascular disease" has it's art-recognized meaning, which includes hypertension, congestive heart failure, stroke, myocardial infarction, neurogenic peripheral vascular disease, obstructive peripheral vascular disease, and migraine. The molecules of the present invention are preferably used in conjunction with the methods of the present invention, which are discussed in detail below.

The molecules of the present invention will preferably be "biologically active" with respect to either a structural attribute, such as the capacity of a nucleic acid to hybridize to another nucleic acid molecule or to be used by a polymerase as a primer. Alternatively, such an attribute may be catalytic, and thus involve the capacity of the agent to mediate a chemical reaction or response.

A preferred class of molecules of the present invention comprise β-adrenergic receptor molecules. Preferably, β-adrenergic receptor molecules will be $\beta_1$-adrenergic receptor molecules or $\beta_2$-adrenergic receptor molecules.

Such molecules may be either DNA or RNA, single-stranded or double-stranded. Such molecules may also be fragments, portions, and segments thereof and molecules, such as oligonucleotides, that specifically hybridize to β-adrenergic receptor nucleic acid molecules. Such molecules may be isolated, derived, or amplified from a biological sample. Alternatively, the molecules of the present invention may be chemically synthesized. The term "isolated" as used herein refers to the state of being substantially free of other material such as nucleic acids, proteins, lipids, carbohydrates, or other materials such as cellular debris or growth media with which the target polynucleotide, primer oligonucleotide, or allele-specific oligonucleotide may be associated. Typically, the term "isolated" is not intended to refer to a complete absence of these materials. Neither is the term "isolated" generally intended to refer to water, buffers, or salts, unless they are present in amounts that substantially interfere with the methods of the present invention. The term "biological sample" as used herein refers to any material containing nucleic acid, either DNA or RNA. Generally, such material will be in the form of a blood sample, tissue sample, cells, bacteria, histology section, or buccal swab, either fresh, fixed, frozen, or embedded in paraffin.

The term "oligonucleotide" as used herein is defined as a polynucleotide molecule comprised of less than about 100 nucleotides. Preferably, oligonucleotides are between 10 and 35 nucleotides in length. Most preferably, oligonucleotides are 15 to 30 nucleotides in length. The exact length of a particular oligonucleotide, however, will depend on many factors, which in turn depend on the ultimate function or use of the oligonucleotide. Short primer molecules generally require lower temperatures to form sufficiently stable hybrid complexes with the template.

Oligonucleotides, such as primer oligonucleotides are preferably single stranded, but may alternatively be double stranded. If double stranded, the oligonucleotide is generally first treated to separate its strands before being used for hybridization purposes or being used to prepare extension products. Preferably, the oligonucleotide is an oligodeoxyribonucleotide. Oligonucleotides may be synthesized chemically by any suitable means known in the art or derived from a biological sample, as for example, by restriction digestion. The source of the oligonucleotides is not essential to the present invention. Oligonucleotides may be labeled, according to any technique known in the art, such as with radiolabels, fluorescent labels, enzymatic labels, proteins, haptens, antibodies, sequence tags, etc. The term "nucleotide" as used herein is intended to refer to ribonucleotides, deoxyribonucleotides, acyclic derivatives of nucleotides, and functional equivalents thereof, of any phosphorylation state. Functional equivalents of nucleotides are those that act as a substrates for a polymerase as, for example, in an amplification method. Functional equivalents of nucleotides are also those that may be formed into a polynucleotide that retains the ability to hybridize in a sequence specific manner to a target polynucleotide.

Such oligonucleotides may be used as probes of a nucleic acid sample, such as genomic DNA, mRNA, or other suitable sources of nucleic acid. For such purposes, the oligonucleotides must be capable of specifically hybridizing to a target polynucleotide or βAR nucleic acid molecule. As used herein, two nucleic acid molecules are said to be capable of specifically hybridizing to one another if the two molecules are capable of forming an anti-parallel, double-stranded nucleic acid structure under hybridizing conditions, whereas they are substantially unable to form a double-stranded structure when incubated with a non-βAR nucleic acid molecule under the same conditions. A nucleic acid molecule is said to be the "complement" of another nucleic acid molecule if it exhibits complete complementarity. As used herein, molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described, for example, by Sambrook, J., et al., (In: *Molecular Cloning, a Laboratory Manual, 2nd Edition*, Cold Spring Harbor Press, Cold Spring Harbor, N.Y. (1989)), and by Haymes, B. D., et al. (In: *Nucleic Acid Hybridization, A Practical Approach*, IRL Press, Washington, D.C. (1985)), both herein incorporated by reference). Departures from complete complementarity are therefore permissible, as long as such departures do not completely preclude the capacity of the molecules to form a double-stranded structure. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith for the purposes employed. However, for detection purposes, particularly using labeled sequence-specific probes, the primers typically have exact complementarity to obtain the best results.

Thus, for an oligonucleotide to serve as an allele-specific oligonucleotide, it must generally be complementary in sequence and be able to form a stable double-stranded structure with a target polynucleotide under the particular environmental conditions employed. The term "allele-specific oligonucleotide" refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism. As will be appreciated by those in the art, allele-specific is not meant to denote an absolute condition. Allele-specificity will depend upon a variety of environmental conditions, including salt and formamide concentrations, hybridization and washing conditions and stringency. Depending on the sequences being analyzed, one or more allele-specific oligonucleotides may be employed for each target polynucleotide. Preferably, allele-specific oligonucleotides will be completely complementary to the target polynucleotide. However, departures from complete complementarity are permissible.

In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration incubation temperatures; and incubation times. The terms "primer" or "primer oligonucleotide" as used herein refer to an oligonucleotide as defined herein, which is capable of acting as a point of initiation of synthesis when placed under conditions in which synthesis of a primer extension product which is complementary to a nucleic acid strand is induced, as for example, in a PCR reaction. As with non-primer oligonucleotides, primer oligonucleotides may be labeled, according to any technique known in the art, such as with radiolabels, fluorescent labels, enzymatic labels, proteins, haptens, antibodies, sequence tags, etc.

In performing the methods of the present invention, the oligonucleotides or the target polynucleotide may be either in solution or affixed to a solid support. Generally, allele-specific oligonucleotides will be attached to a solid support, though in certain embodiments of the present invention allele-specific oligonucleotides may be in solution. In some such embodiments, the target polynucfeotide is preferably bound to a solid support. In those embodiments where the allele-specific oligonucleotides or the target polynucleotides are attached to a solid support, attachment may be either covalent or non-covalent. Attachment may be mediated, for example, by antibody-antigen-type interactions, poly-L-Lys, streptavidin or avidin-biotin, salt-bridges, hydrophobic interactions, chemical linkages, UV cross-linking, baking, etc. In addition, allele-specific oligonucleotides may be synthesized directly on a solid support or attached to the solid support subsequent to synthesis. In a preferred embodiment, allele-specific oligonucleotides are affixed a solid support such that a free 3'-OH is available for polymerase-mediated primer extension.

Suitable solid supports for the present invention include substrates constructed of silicon, glass, plastic (polystyrene, nylon, polypropylene, etc.), paper, etc. Solid supports may be formed, for example, into wells (as in 96-well dishes), plates, slides, sheets, membranes, fibers, chips, dishes, and beads. In certain embodiments of the present invention, the solid support is treated, coated, or derivatized so as to facilitate the immobilization of an allele-specific oligonucleotide or a target polynucleotide. Preferred treatments include coating, treating, or derivatizing with poly-L-Lys, streptavidin, antibodies, silane derivatives, low salt, or acid.

Uses of the Polymorphisms and Molecules of the Present Invention

The polymorphisms and molecules of the present invention are most preferably used in the diagnosis and prognosis of cardiovascular diseases, obesity, and diabetes. Alternatively, the polymorphisms and molecules of the present invention are used to predict an individual's responsiveness to synthetic agonists and antagonists, i.e., they may be used to assist in determining an appropriate treatment regimen for the above-mentioned diseases.

Preferably, the identity of at least one polymorphic site in a β-adrenergic receptor molecule is determined. Generally, in performing the methods of the present invention, the identity of more than one polymorphic site is determined. In some preferred embodiments, the identity of between about two and about six polymorphic sites is determined, though the identification of other numbers of sites is also possible. In a highly preferred embodiment of the present invention, at least one polymorphism in both a $\beta_1 AR$ and a $\beta_2 AR$ is identified. In other preferred embodiments of the present invention, the identity of at least one polymorphism is determined in either a $\beta_1 AR$ or a $\beta_2 AR$, but not both. In another preferred embodiment of the present invention, the identity of four polymorphic sites in a $\beta_2 AR$ and two polymorphic sites in a $\beta_1 AR$ is determined.

Most preferably, the polymorphisms and molecules of the present invention are utilized in determining the identity of at least one polymorphic site of a $\beta_1 AR$ or a $\beta_2 AR$ gene and using that identity as a predictor for the development of, or the clinical course of, at least one cardiovascular disease. Examples of cardiovascular diseases include hypertension, congestive heart failure, stroke, myocardial infarction, neurogenic and obstructive peripheral vascular disease, and migraine. The invention is additionally directed to the use of $\beta_1 AR$ and $\beta_2 AR$ polymorphisms as predictors of the development of, or the clinical course of, obesity and/or diabetes.

Quite apart from such usage, the polymorphisms and molecules of the present invention may be used to diagnose or predict an individual's sensitivity or responsiveness to administration of synthetic βAR agonists and antagonists. Certain individuals exhibit a decreased responsiveness to such compounds (S. B. Ligget, In: *The Genetics of Asthma*, S. B. Ligget et al., eds. (1995)). The present invention may therefore be employed to diagnose or predict such sensitivity, as well as to guide selection of appropriate patient medication.

Methods of the Present Invention

The polymorphisms of the present invention may be characterized using any of a variety of suitable methods. Suitable methods comprise direct or indirect sequencing methods, restriction site analysis, hybridization methods, nucleic acid amplification methods, gel migration methods, the use of antibodies that are specific for the proteins encoded by the different alleles of the polymorphism, or by other suitable means. Alternatively, Many such methods are well known in the art and are described, for example in T. Maniatis et al., *Molecular Cloning, a Laboratory Manual*, 2nd Edition, Cold Spring Harbor Press, Cold Spring Harbor, N.Y. (1989), J. W. Zyskind et al., *Recombinant DNA Laboratory Manual*, Academic Press, Inc., New York (1988), and in R. Elles, *Molecular Diagnosis of Genetic Diseases*, Humana Press, Totowa, N.J. (1996), each herein incorporated by reference.

Identification methods may be of either a positive-type or a negative-type. Positive-type methods determine the identity of a nucleotide contained in a polymorphic site, whereas negative-type methods dermine the identity of a nucleotide not present in a polymorphic site. Thus, a wild-type site may be identified either as wild-type or not mutant. For example, at a biallelic polymorphic site where the wild-type allele contains an adenine and the mutant allele contains a cytosine, a site may be positively determined to be either adenine or cytosine or negatively determined to be not adenine (and thus cytosine) or not cytosine (and thus adenine). As another example, in hybridization-based assay, a target polynucleotide containing a mutated site may be identified positively by hybridizing to an allele-specific oligonucleotide containing the the mutated site or negatively, by failing to hybridize to a wild-type allele-specific oligonucleotide. Similarly, a restriction site may be determined to be present or lacking.

Direct Sequencing Methods of the Present Invention

Direct sequencing by methods such as dideoxynucleotide sequencing (Sanger), cycle sequencing, or Maxam-Gilbert sequencing are examples of suitable methods for determining the identity of a nucleotide at a polymorphic site of a target polynucleotide. Such methods are widely known in the art and are discussed at length, in the above-cited texts.

Both the dideoxy-mediated method and the Maxam-Gilbert method of DNA sequencing require the prior isolation of the DNA molecule which is to be sequenced. The sequence information is obtained by subjecting the reaction products to electrophoretic analysis (typically using polyacrylamide gels). Thus, a sample is applied to a lane of a gel, and the various species of nested fragments are separated from one another by their migration velocity through the gel.

The number of nested fragments which can be separated in a single lane is approximately 200–300 regardless of whether the Sanger or the Maxam-Gilbert method is used. Thus, in order to identify a nucleotide at a particular polymorphic site in a target polynucleotide, extraneous sequence information is typically produced. The chief advantage of direct sequencing lies in its utility for locating previously unidentified polymorphic sites.

One of the problems that has encumbered the development of useful assays for genetic polymorphisms is that in many cases, it is desirable to determine the identity of multiple polymorphic loci. This frequently requires sequencing significant regions of the genome or performing multiple assays with an individual patient sample.

Restriction Site Analysis Methods of the Present Invention

Restriction enzymes are specific for a particular nucleotide sequence. In certain embodiments of the present invention, the identity of a nucleotide at a polymorphic site is determined by the presence or absence of a restriction enzyme site. A large number of restriction enzymes are known in the art and, taken together, they are capable of recognizing at least one allele of many polymorphisms. This feature of restriction enzymes may be utilized in a variety of methods for identifying a polymorphic site. Restriction fragment length polymorphism (RFLP) analysis is an example of a suitable method for identifying a polymorphic site with restriction enzymes (Lentes et al., *Nucleic Acids Res.* 16:2359 (1988); and C. K. McQuitty et al., *Hum. Genet.* 93:225 (1994)). In RFLP analysis, at least one target polynucleotide is digested with at least one restriction enzyme and the resultant "restriction fragments" are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays.

Hybridization Methods of the Present Invention

Several suitable hybridization-based methods for identifying a nucleotide at a polymorphic site have been described. Generally, allele-specific oligonucleotides are utilized in performing such hybridization-based methods. Preferably, allele-specific oligonucleotides are chosen that are capable of specifically hybridizing to only one allele of a βAR molecule at a region comprising a polymorphic site. In those embodiments wherein more than one polymorphic site is identified, sets of allele-specific oligonucleotides are preferably chosen that have melting temperatures within 5° C. of each other when hybridizing to their complete complement. Most preferably, such sets of allele-specific oligonucleotides are chosen so as to have melting temperatures within 2° C. of each other. Examples of suitable hybridization methods are described in standard manuals such as Molecular Cloning, A Laboratory Manual (2nd Ed., Sambrook, Fritsch and Maniatis, Cold Spring Harbor); and Current Protocols in Molecular Biology (Eds. Ausubel, Brent, Kingston, More, Feidman, Smith and Stuhl, Greene Publ. Assoc., Wiley-Interscience, NY, N.Y., 1992) or that are otherwise known in the art. Examples of preferred hybridization methods include Southern, northern, and dot blot hybridizations, allele-specific oligonucleotide hybridizations (Hall et al., *The Lancet* 345:1213–1214 (1995)), reverse dot blot hybridizations (Sakai et al., *Nucl. Acids. Res.* 86:6230–6234 (1989)), DNA chip hybridizations (Drmanac et al., U.S. Pat. No. 5,202,231), and hybridizations to allele-specific oligonucleotides.

Macevicz (U.S. Pat. No. 5,002,867), for example, describes a method for deriving nucleic acid sequence information via hybridization with multiple mixtures of oligonucleotide probes. In accordance with such method, the sequence of a target polynucleotide is determined by permitting the target to sequentially hybridize with sets of probes having an invariant nucleotide at one position, and a variant nucleotides at other positions. The Macevicz method determines the nucleotide sequence of the target by hybridizing the target with a set of probes, and then determining the number of sites that at least one member of the set is capable of hybridizing to the target (i.e. the number of "matches"). This procedure is repeated until each member of a sets of probes has been tested.

Polymerase-Mediated Primer Extension Methods of the Present Invention

The "Genetic Bit Analysis" ("GBA") method disclosed by Goelet, P. et al. (WO92/15712, herein incorporated by reference), and discussed below, is a preferred method for determining the identity of a nucleotide at a predetermined polymorphic site in a target polynucleotide. GBA is a method of polymorphic site interrogation in which the nucleotide sequence information surrounding a polymorphic site in a target nucleic acid sequence is used to design an oligonucleotide primer that is complementary to a region immediately adjacent to, but not including, the variable nucleotide in the polymorphic site of the target polynucleotide. The target polynucleotide is isolated from the biological sample and hybridized to the interrogating primer. In some embodiments of the present invention, following isolation, the target polynucleotide may amplified by any suitable means prior to hybridization to the interrogating primer. The primer is extended by a single labeled terminator nucleotide, such as a dideoxynucleotide, using a polymerase, often in the presence of one or more chain terminating nucleoside triphosphate precursors (or suitable analogs). A detectable signal is thereby produced. In some embodiments of the present invention, the oligonucleotdie is bound to a solid support prior to the extension reaction. In other embodiments, the extension reaction is performed in solution and the extended product is subsequently bound to a solid support.

In an alternate sub-embodiment of GBA, the primer is detectably labeled and the:extended terminator nucleotide is modified so as to enable the extended primer product to be bound to a solid support. An example of this would be where the primer is fluorescently labeled and the terminator nucleotide is a biotin-labeled terminator nucleotide and the solid support is coated or derivitized with avidin or streptaviden. In such embodiments, an extended primer would thus be enabled to bind to a solid support and non-extended primers would be unable to bind to the support, thereby producing a detectable signal dependent upon an a successful extension reaction.

Ligase/polymerase mediated genetic bit analysis (U.S. Pat. No. 5,679,524, herein incorporated by reference) is another example of a suitable polymerase mediated primer extension method for determining the identity of a nucleotide at a polymorphic site. Ligase/polymerase GBA utilizes two primers. Generally, one primer is detectably labeled, while the other is designed to be affixed to a solid support. In alternate embodiments of ligase/polymerase GBA, extended nucleotide is detectably labeled. The primers in ligase/polymerase GBA are designed to hybridize to each side of a polymorphic site, such that there is a gap comprising the polymorphic site. Only a successful extension reaction, followed by a successful ligation reaction enables the production of the detectable signal. The method offers the advantages of producing a signal with considerably lower background than is possible by methods employing only hybridization or primer extension alone.

Cohen, D. et al. (PCT Application WO91/02087) describes another example of a suitable method for determining the identity of a polymorphic site, wherein dideoxynucleotides are used to extend a single primer by a single nucleotide in order to determine the sequence at a desired locus. Dale et al. (PCT Application WO90/09455) discloses a method for sequencing a "variable site" using a primer in conjunction with a single dideoxynucleotide species. The method of Dale et al. further discloses the use of multiple primers and the use of a separation element. Ritterband, M., et al., (PCT Application WO95/17676) describes an apparatus for the separation, concentration and detection of such target molecules in a liquid sample. Cheeseman, P. C. (U.S. Pat. No. 5,302,509) describes a related method of determining the sequence of a single stranded DNA molecule. The method of Cheeseman employs fluorescently labeled 3'-blocked nucleotide triphosphates with each base having a different fluorescent label.

Wallace et al. (PCT Application WO89/10414) describes multiple PCR procedures which can be used to simultaneously amplify multiple regions of a target by using allele specific primers. By using allele specific primers, amplification can only occur if a particular allele is present in a sample.

Several other suitable primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvänen, A.-C., et al., *Genomics* 8:684–692 (1990); Kuppuswamy, M. N. et al., *Proc. Natl. Acad. Sci. (U.S.A.)* 88:1143–1147 (1991); Prezant, T. R. et al., *Hum. Mutat.* 1:159–164 (1992); Ugozzoli, L. et al., *GATA* 9:107–112 (1992); Nyrén, P. et al., *Anal. Biochem.* 208:171–175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide will result in signals that are proportional to the length of the run (Syvänen, A.-C., et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA method.

Amplification Methods of the Present Invention

In certain embodiments of the present invention, the detection of polymorphic sites in a target polynucleotide may be facilitated through the use of nucleic acid amplification methods. Such methods may be used to specifically increase the concentration of the target polynucleotide (i.e., sequences that span the polymorphic site, or include that site and sequences located either distal or proximal to it). Such amplified molecules can be readily detected by gel electrophoresis, or other means.

The most preferred method of achieving such amplification employs PCR (e.g., Mullis, et al., U.S. Pat. No. 4,965,188), using primer pairs that are capable of hybridizing to the proximal sequences that define or flank a polymorphic site in its double-stranded form.

In some embodiments of the present invention, the amplification method is itself a method for determining the identity of a polymorphic site, as for example, in allele-specific PCR (J. Turki et al., *J. Clin. Invest.* 95:1635–1641 (1995)). In allele-specific PCR, primer pairs are chosen such that amplification is dependent upon the input template nucleic acid containing the polymorphism of interest. In such embodiments, primer pairs are chosen such that at least one primer is an allele-specific oligonucleotide primer. In some sub-embodiments of the present invention, allele-specific primers are chosen so that amplification creates a restriction site, facilitating identification of a polymorphic site. In other embodiments of the present invention, amplification of the target polynucleotide is by multiplex PCR (Wallace et al. (PCT Application WO89/10414)). Through the use of multiplex PCR, a multiplicity of regions of a target polynucleotide may be amplified simultaneously. This is particularly advantageous in those embodiments wherein greater than a single polymorphism is detected.

In lieu of PCR, alternative methods, such as the "Ligase Chain Reaction" ("LCR") may be used (Barany, F., *Proc. Natl. Acad. Sci. (U.S.A.)* 88:189–193 (1991)). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resultant product serves as a template in subsequent amplification cycles, resulting in an exponential amplification of the desired sequence.

In accordance with the present invention, LCR can be performed using oligonucleotides having sequences derived from the same strand, located proximal and distal to the polymorphic site. In one embodiment, either oligonucleotide is designed so as to include the actual polymorphic site of the polymorphism. In such an embodiment, the reaction conditions are selected such that the oligonucleotides can be ligated together only if the target molecule contains the specific nucleotide in the polymorphic site that is complementary to the polymorphic site present on the oligonucleotide.

In an alternative embodiment, the oligonucleotides will not include the polymorphic site, such that when they hybridize to the target molecule, a "gap" of at least one nucleotide is created (see, Segev, D., PCT Application WO90/01069). This gap is then "filled" with complementary dNTPs (as mediated by DNA polymerase), or by an additional pair of oligonucleotides. Thus, at the end of each cycle, each single strand has a complement capable of serving as a target during the next cycle and exponential amplification of the desired sequence is obtained.

The "Oligonucleotide Ligation Assay" ("OLA") (Landegren, U. et al., *Science* 241:1077–1080 (1988)) shares certain similarities with LCR and is also a suitable method for analysis of polymorphisms. The OLA protocol uses two oligonucleotides, which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson, D. A. et al. have described a nucleic acid detection assay that combines attributes of PCR and OLA (Nickerson, D. A. et al., *Proc. Natl. Acad. Sci. (U.S.A.)* 87:8923–8927 (1990)). In this method, PCR is used to achieve the exponential amplification of target DNA, which is then detected using OLA.

Schemes based on ligation of two (or more) oligonucleotides in the presence of nucleic acid having the sequence of the resulting "di-oligonucleotide", thereby amplifying the di-oligonucleotide, are known (Wu, D. Y. et al., *Genomics* 4:560 (1989); Adams, C., WO94/03630), and are also suitable methods for the purposes of the present invention.

Other known nucleic acid amplification procedures, such as transcription-based amplification systems (Malek, L. T. et al., U.S. Pat. No. 5,130,238; Davey, C. et al., European Patent Application 329,822; Schuster et al., U.S. Pat. No. 5,169,766; Miller, H. I. et al., PCT Application WO89/06700; Kwoh, D. et al., *Proc. Natl. Acad. Sci. (U.S.A.)* 86:1173 (1989); Gingeras, T. R. et al., PCT Application WO88/10315)), or isothermal amplification methods (Walker, G. T. et al., *Proc. Natl. Acad. Sci. (U.S.A.)* 89:392–396 (1992)) may also be used.

Gel Migration Methods of the Present Invention

Single, strand conformational polymorphism (SSCP; M. Orita et al., *Genomics* 5:874–879 (1989); Humphries et al., In: *Molecular Diagnosis of Genetic Diseases*, R. Elles, ed. pp321–340 (1996)) and temperature gradient gel electrophoresis (TGGE; R.M. Wartell et al., *Nucl. Acids Res.* 18:2699–2706 (1990)) are examples of suitable gel migration-based methods for determining the identity of a polymorphic site. In SSCP, a single strand of DNA will adopt a conformation that is uniquely dependent of its sequence composition. This conformation is usually different, if even a single base is changed. Thus, certain embodiments of the present invention, SSCP may be utilized to identify polymorphic sites, as wherein amplified products (or restriction fragments thereof) of the target polynucleotide are denatured, then run on a non-denaturing gel. Alterations in the mobility of the resultant products is thus indicative of a base change. Suitable controls and knowledge of the "normal" migration patterns of the wild-type alleles may be used to identify polymorphic variants.

TGGE is a related procedure, except that the nucleic acid sample is run on a denaturing gel. In embodiments of the present invention utilizing TGGE to identify a polymorphic site, the amplified products (typically PCR products) are electrophoresed over denaturing polyacrylamide gel, wherein the temperature gradient is optimized for separation of the target polynucleotide segments (E. Reihsaus et al., *Am. J. Respir. Cell Mol. Biol.* 8:334–339 (1993), herein incorporated by reference). This method is able to detect single base changes in the target polynucleotide sequence.

Having now generally described the invention, the same may be more readily understood through the following reference to the following examples, which are provided by way of illustration and are not intended to be limiting of the present invention unless specified.

EXAMPLE I

Frequency and distribution of $\beta_1AR$ and $\beta_2AR$ gene polymorphisms in Patients with Congestive Heart Failure (CHF)

A group of normal subjects and patients with early and late CHF are analyzed for $\beta_1AR$ and $\beta_2AR$ gene defects and then clinically followed for a five year period. This allows a determination as to which mutations of these genes play a major role in the pathogenesis of cardiovascular diseases or influence their clinical course.

Patient Selection Three groups of patients are studied: normals, those with heart failure due to early (N.Y.H.A. functional class I–II) and those with late (N.Y.H.A. functional class III–IV) CHF. Control groups consist of normal volunteers with no history of any chronic illness, no family history of hypertension, cardiac or lung disease. In some studies, samples of normal control hearts are also obtained from normal explanted donor hearts not used for transplantation.

General Approach Groups of normal subjects and those with early and late CHF (as described above) are selected. Baseline echocardiograms, ECG's, exercise stress tests and symptom scoring are obtained. Blood is drawn for analysis of $\beta_1AR$ and $\beta_2AR$ gene polymorphisms by GBA as in Example II. Patients and normal subjects are then followed over the course of five years to delineate the progression of symptoms and objective measurements of cardiovascular function over time. The above studies and symptom scoring are repeated yearly. Initially, those involved in the genetic analysis are blinded as to patients' clinical conditions. Those performing the above described cardiac function tests and symptom scoring, as well as the physicians taking care of these patients, are not informed of the $\beta_1AR$ or $\beta_2AR$ genotypes. As patients are followed, the condition of some patients progress in severity. From the initial gene analysis, it is determined which $\beta_1AR$ or $\beta_2AR$ mutations play a specific causal role in DCM. Further, the nature of specific $\beta AR$ gene defects is then correlated with the clinical course of the disease.

EXAMPLE II

Genetic Bit Analysis of $\beta_1$- and $\beta_2$-Adrenergic Receptor Polymorphisms Peripheral blood lymphocytes (PBL) are isolated from human whole blood by ficol/hypaque centrifugation. Target genomic DNA is isolated from PBL using the SDS/Proteinase K procedure (Maniatis, T. Molecular Cloning, A Laboratory Manual, Cold Spring Harbor Laboratory Press, Cold Spring Harbor, 1989). Oligonucleotides are prepared by solid-phase synthesis according to the methods of Skerra, Vosberg et al., and Noronha et al. (A. Skerra *Nucleic Acids Research* 20:3551–3554 (1992); H. P. Vosberg et al., *Biochemistry* 16:3633 (1977); C. M. de Noronha et al., *PCR Methods Appl.* 2:131–6 (1992); T. Nikiforov U.S. Pat. No. 5,518,900).

Target polynucleotide is amplified from the patient genomic DNA by multiplex PCR, using primers sufficient for amplifying regions in comprising nucleotides 145 and 1165 of a $\beta_1AR$ molecule and nucleotides 46, 79, 100, and 491 of a $\beta_2AR$ molecule. One set of two primers is used for amplifying each polymorphic site-containing region. Thus, 24 different PCR primers are used. Primers are chosen such that amplified products are each about 200 nucleotides in length.

Allele-specific oligonucleotides are synthesized that are each specific for one of the following polymorphisms in a $\beta_1AR$: Ser49, Gly49, Gly389, Arg389. Allele-specific oligonucleotides are also synthesized that are each specific for one of the following polymorphisms in a $\beta_2AR$: Arg16, Gly16, Gln27, Glu27, Val34, Met34, Thr164, and Ile164.

Each allele-specific oligonucleotide, twelve in all, is amino-derivatized at its 5' end, using Aminolink 2 (Applied Biosystems) according to the manufacturer's recommendations.

Each 5'-amino-modified, allele-specific oligonucleotide is then covalently coupled in duplicate to individual wells of a 96-well dish (Nunc) by incubating the oligonucleotides in 50 μl of 3 mM sodium phosphate buffer, pH 6, 20 mM 1-ethyl-3-(3-dimethylaminoproply)-carbodiimide (EDC) overnight at room temperature. After coupling, the plate is washed three times with 10 mM Tris pH 7.5/150 mM NaCl/0.05% Tween-20.

20 μl of hybridization buffer is added to several empty wells as a control. 20 μl of target polynucleotide solution in hybridization buffer is added to each of the wells containing bound allele-specific oligonucleotides and several empty wells. As a further control, 20 μl of target polynucleotide solution in hybridization buffer is added to several wells containing no bound allele-specific oligonucleotides. The dish is covered and incubated at 55° C. for 30 minutes tod allow hybridization of the target DNA to the immobilized oligonucleotides. The wells are then washed.

20 μl of a polymerase extension mix, containing four distinguishable, fluorescently labeled dideoxynucleotide triphosphates (corresponding to ddATP, ddTTP, ddGTP, ddCTP), $MnCl_2$, and modified T7 DNA polymerase is then added to each well and the reaction is incubated at room temperature.

Each of the bound primers are extended by a single fluorescent labeled chain terminator ddNTP by the polymerase. The enzyme-mediated fluorescence signal is then obtained using a Cytofluor II fluorescent plate reader. The results positively determines the identify of each of the polymorphic sites.

EXAMPLE III

$\beta_2$AR Polymorphisms and Risk for Death or Transplant 279 patients with heart failure are enrolled and clinically followed as in Example I. Blood is drawn from each individual and genotyped, as per Example II, using primers specific for the Thr164, Ile164, Arg16, and Gly16 polymorphisms of the $\beta_2$AR. Preliminary results for 279 patients with heart failure are shown in FIGS. 1 and 2.

FIG. 1 shows the relationship between survival and number of follow-up days since enrollment in the study. Individuals with the Ile164 $\beta_2$AR polymorphism have a greater chance of either death or requirement for heart transplant, when compared to those the Thr164 (wild-type) receptor. The relative risk is 4.54 with a significance of p=0.0014.

Figure 2:
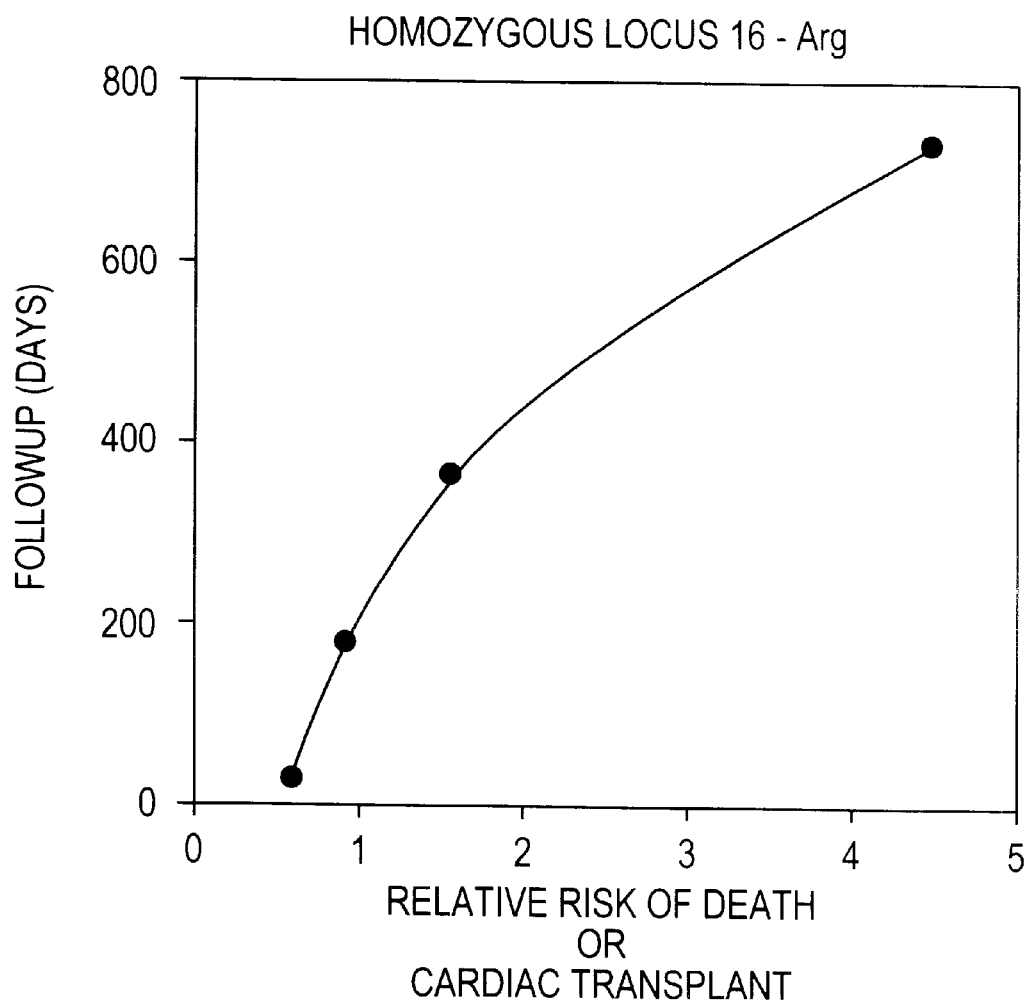
FIG. 2 provides a graph of the relative risk for either death or heart transplant, plotted against the number of follow-up days since enrollment. An experiment with involving 279 patients with heart failure is shown.

FIG. 2 shows the relative risk of death or transplant associated with the Arg16 $\beta_2$AR polymorphism. In FIG. 2, the relative risk of death or transplant is plotted against the number of follow-up days for the Arg16 $\beta_2$AR polymorphism. At very early time points, the risk is not significant. However, with increasing time, the risk value approaches 5.

EXAMPLE IV

Affect of βAR polymorphisms on Blood Pressure in Individuals Without Heart Failure Blood is drawn from 20 volunteers without heart failure and genotyped as per Example II, using primers specific for the Gly16 and Arg16 polymorphisms of the $\beta_2$AR. Blood pressure is then measured at rest. The results are shown in Table 3. As can be seen, the Gly16 polymorphism is associated with a significantly higher diastolic and mean arterial blood pressure (MAP).

TABLE 3

| Affect of Arg16/Gly16 Polymorphism on Blood Pressure | | |
| --- | --- | --- |
| Blood Pressure (mmHg) | Arg16 | Gly16 |
| Diastolic Blood Pressure | 58 ± 4 | 73 ± 3* |
| Mean Arterial Pressure | 78 ± 5 | 88 ± 4* |
| Systolic Blood Pressure | 117 ± 6 | 120 ± 4 |

*$p < 0.01$ compared to individuals with Arg16.

EXAMPLE V

Correlation of βAR Gene Defects with In Vivo Cardiac Function

Blood is drawn and patients are genotyped as per Example II. In order to correlate βAR gene defects with in vivo cardiac βAR function, patients with selected βAR gene defects are studied hemodynamically to determine the functional responsiveness of cardiac βAR to infused dobutamine.

EXAMPLE VI

βAR Expression and Function in Patients with CHF

Blood is drawn and patients are genotyped as per Example II. The presence of genetic variants of the $\beta_1$AR or $\beta_2$AR in patients with CHF is correlated with receptor expression and function in tissue obtained from left endomyocardial biopsies.

While the invention has been described in connection with specific embodiments thereof, it will be understood that it is capable of further modifications and this application is intended to cover any variations, uses, or adaptations of the invention following, in general, the principles of the invention and including such departures.from the present disclosure as come within known or customary practice within the art to which the invention pertains and as may be applied to the essential features hereinbefore set forth and as follows in the scope of the appended claims.

What is claimed is:

1. A method of determining survival rate in a subject with congestive heart failure, comprising:
   a. obtaining a sample comprising a polynucleotide encoding a beta-2-adrenergic receptor molecule or fragment of the polynucleotide from the subject; and
   b. detecting in the sample a polymorphic site at nucleotide position 491 of the polynucleotide or fragment of the polynucleotide, wherein a thymine at position 491 indicates a decreased survival rate, thereby determining survival rate in the subject with congestive heart failure.

2. A method according to claim 1, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

3. A method of determining survival rate in a subject with congestive heart failure, comprising:
   a. obtaining a sample comprising a polynucleotide encoding a beta-2-adrenergic receptor molecule or fragment of the polynucleotide from the subject; and b. detecting in the sample a polymorphic site at nucleotide position 491 of the polynucleotide or fragment of the polynucleotide, wherein a cytosine at position 491 indicates an increased survival rate, thereby determining survival rate in the subject with congestive heart failure.

4. A method according to claim 3, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligaseipolymerase genetic bit analysis.

5. A method of determining whether a subject is at increased risk for elevated arterial blood pressure, comprising:
   a. obtaining a sample comprising a polynucleotide encoding a beta-2-adrenergic receptor molecule or fragment of the polynucleotide from the subject; and
   b. detecting in the sample a polymorphic site at nucleotide position 46 of the polynucleotide or fragment of the polynucleotide, wherein a guanine at nucleotide position 46 indicates increased risk for elevated arterial blood pressure.

6. A method according to claim 5, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

7. A method of determining whether a subject with heart failure is in need of a heart transplant, comprising:
   a. obtaining a sample comprising a polynucleotide encoding a beta-2-adrenergic receptor molecule or fragment of the polynucleotide from the subject; and
   b. detecting in the sample a polymorphic site at nucleotide position 491 of the polynucleotide or fragment of the polynucleotide, wherein a thymine at nucleotide position 491 indicates need for the heart transplant, thereby determining whether the subject with heart failure is in need of the heart transplant.

8. A method according to claim 7, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

9. A method of determining whether a subject with heart failure is in need of a heart transplant, comprising:
   a. obtaining a sample comprising a polynucleotide encoding a beta-1-adrenergic receptor molecule or fragment of the polynucleotide from the subject; and
   b. detecting in the sample a polymorphic site at nucleotide position 1165 of the polynucleotide or fragment of the polynucleotide, wherein a cytosine at nucleotide position 1165 indicates need for the heart transplant, thereby determining whether the subject with heart failure is in need of a heart transplant.

10. A method according to claim 9, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

11. A method of determining whether a subject with heart failure is in need of a heart transplant or at increased risk of death, comprising:
   a. obtaining a sample comprising a polynucleotide encoding a beta-2-adrenergic receptor molecule or fragment of the polynucleotide from the subject; and
   b. detecting in the sample a polymorphic site at nucleotide position 46 of the polynucleotide or fragment of the polynucleotide, wherein an adenine at nucleotide position 46 indicates need for the heart transplant or at increased risk of death, thereby determining whether the subject with heart failure is in need of the heart transplant or at increased risk of death.

12. A method according to claim 11, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

13. A method of determining survival rate in a subject with congestive heart failure, comprising:
   (a) obtaining a sample comprising a complement or fragment of the complement of a polynucleotide encoding a beta-2-adrenergic receptor molecule from the subject; and
   (b) detecting in the sample a polymorphic site at nucleotide position 491 of the complement or fragment of the complement, wherein an adenine at position 491 of the complement or fragment of the complement indicates a decreased survival rate, thereby determining survival rate in the subject with congestive heart failure.

14. A method according to claim 13, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

15. A method of determining survival rate in a subject with congestive heart failure, comprising:
   (a) obtaining a sample comprising a complement or fragment of the complement of a polynucleotide encoding a beta-2-adrenergic receptor molecule from the subject; and
   (b) detecting in the sample a polymorphic site at nucleotide position 491 of the complement or fragment of the complement, wherein a guanine at position 491 of the complement or fragment of the complement indicates an increased survival rate, thereby determining survival rate in the subject with congestive heart failure.

16. A method according to claim 15, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

17. A method of determining whether a subject is at increased risk for elevated arterial blood pressure, comprising:
   (a) obtaining a sample comprising a complement or fragment of the complement of a polynucleotide encoding a beta-2-adrenergic receptor molecule from the subject; and
   (b) detecting in the sample a polymorphic site at nucleotide position 46 of the complement or fragment of the complement, wherein an cytosine at nucleotide position 46 of the complement or fragment of the complement indicates increased risk for elevated arterial blood pressure.

18. A method according to claim 17, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

19. A method of determining whether a subject with heart failure is in need of a heart transplant, comprising:
(a) obtaining a sample comprising a complement or fragment of the complement of a polynucleotide encoding a beta-2-adrenergic receptor molecule from the subject; and
(b) detecting in the sample a polymorphic site at nucleotide position 491 of the complement or fragment of the complement, wherein an adenine at nucleotide position 491 of the complement or fragment of the complement indicates need for the heart transplant.

20. A method according to claim 19, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

21. A method of determining whether a subject with heart failure is in need of a heart transplant, comprising:
(a) obtaining a sample comprising a complement or fragment of the complement of a polynucleotide encoding a beta-1-adrenergic receptor molecule from the subject; and
(b) detecting in the sample a polymorphic site at nucleotide position 1165 of the complement or fragment of the complement, wherein a guanine at nucleotide position 1165 of the complement or fragment of the complement indicates the need for a heart transplant.

22. A method according to claim 21, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

23. A method of determining whether a subject with heart failure is in need of a heart transplant or at increased risk of death, comprising:
(a) obtaining a sample comprising a complement or fragment of the complement of a polynucleotide encoding a beta-2-adrenergic receptor molecule from the subject; and
(b) detecting in the sample a polymorphic site at nucleotide position 46 of the complement or fragment of the complement, wherein a thymine at nucleotide position 46 of the complement or fragment of the complement indicates the need for a heart transplant or the increased risk of death.

24. A method according to claim 23, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis.

25. An isolated polynucleotide of a nucleotide sequence encoding a beta-1-adrenergic receptor comprising a cytosine at nucleotide position 1165.

26. An isolated polynucleotide of a nucleotide sequence encoding a beta-1-adrenergic receptor useful for determining whether a subject with heart failure is in need of a heart transplant comprising a cytosine at nucleotide position 1165.

27. An isolated polynucleotide complementary to a nucleotide sequence encoding a beta-1 adrenergic receptor comprising a guanine at nucleotide position 1165.

28. An isolated polynucleotide or fragment thereof of a nucleotide sequence encoding a beta-1 adrenergic receptor comprising a guanine at nucleotide position 1165.

29. A fragment of an isolated polynucleotide of a nucleotide sequence encoding a beta-1 adrenergic receptor comprising a cytosine at nucleotide position 1165.

30. A fragment of an isolated polynucleotide of a nucleotide sequence encoding a beta-1 adrenergic receptor comprising a cytosine at nucleotide position 1165 useful in determining whether a subject with heart failure is in need of a heart transplant.

31. A probe that specifically hybridizes to a cytosine at nucleotide position 1165 of a nucleotide sequence encoding a beta-1 adrenergic receptor.

32. An oligonucleotide primer that hybridizes to an isolated polynucleotide at a region flanking nucleotide position 1165 of a nucleotide sequence encoding a beta-1 adrenergic receptor, wherein the polynucleotide comprises a cytosine at nucleotide position 1165.

33. An oligonucleotide primer according to claim 32, for determining whether a subject with heart failure is in need of a heart transplant.

34. An oligonucleotide primer according to claim 32, wherein the primer specifically hybridizes up to 100 nucleotides from the 3' or 5' end of nucleotide position 1165.

35. An oligonucleotide primer according to claim 32, wherein the primer contains up to 100 nucleotides.

36. An oligonucleotide primer according to claim 32, wherein the primer is immediately adjacent to either the 5' or 3' end of nucleotide position 1165.

37. An oligonucleotide primer according to claim 32, wherein the primer has up to 100 nucleotides and is on the 5' end of nucleotide position 1165.

38. An oligonucleotide primer according to claim 32, wherein the primer has up to 100 nucleotides and is on the 3' end of nucleotide position 1165.

39. A method of detecting a polymorphic site occurring in a polynucleotide encoding a beta-1 adrenergic receptor molecule, comprising: obtaining a sample comprising the polynucleotide or fragment of the polynucleotide; and detecting in the sample the polymorphic site at position 1165 of the polynucleotide or fragment of the polynucleotide, thereby detecting in,:the sample the nucleotide at the polymorphic site at nucleotide position 1165 of the polynucleotide encoding a beta-1 adrenergic receptor.

40. A method according to claim 39, wherein the polymorphic site comprises guanine or cytosine at nucleotide position 1165.

41. A method according to claim 39, wherein the detection of the polymorphic site is by chain terminating sequencing, restriction digestion, allele-specific polymerase reaction, single-stranded conformational polymorphism analysis, genetic bit analysis, temperature gradient gel electrophoresis, ligase chain reaction, or ligasel/polymerase genetic bit analysis.

42. A method according to claim 41, wherein the detection of the polymorphic site is by genetic bit analysis.

\* \* \* \* \*

UNITED STATES PATENT AND TRADEMARK OFFICE
CERTIFICATE OF CORRECTION

PATENT NO. : 6,498,009 B1  
APPLICATION NO. : 08/948643  
DATED : December 24, 2002  
INVENTOR(S) : Stephen B. Liggett Page 1 of 1

It is certified that error appears in the above-identified patent and that said Letters Patent is hereby corrected as shown below:

In the Specification

Add the following paragraph after paragraph [001], column 1, line 3:

This invention was made with government support under HL045967 and HL052318 awarded by National Institutes of Health. The government has certain rights in the invention.

Signed and Sealed this  
Twelfth Day of May, 2015

Michelle K. Lee  
*Director of the United States Patent and Trademark Office*